US009510795B2

(12) United States Patent
Takemoto et al.

(10) Patent No.: US 9,510,795 B2
(45) Date of Patent: Dec. 6, 2016

(54) RADIOGRAPHIC X-RAY EQUIPMENT

(71) Applicant: THE YOSHIDA DENTAL MFG. CO., LTD., Tokyo (JP)

(72) Inventors: Terumi Takemoto, Tokyo (JP); Takeshi Tomoe, Tokyo (JP)

(73) Assignee: THE YOSHIDA DENTAL MFG. CO., LTD., Tokyo (JP)

(*) Notice: Subject to any disclaimer, the term of this patent is extended or adjusted under 35 U.S.C. 154(b) by 247 days.

(21) Appl. No.: 14/378,508

(22) PCT Filed: Feb. 7, 2013

(86) PCT No.: PCT/JP2013/052946
§ 371 (c)(1),
(2) Date: Aug. 13, 2014

(87) PCT Pub. No.: WO2013/125361
PCT Pub. Date: Aug. 29, 2013

(65) Prior Publication Data
US 2015/0036800 A1 Feb. 5, 2015

(30) Foreign Application Priority Data
Feb. 21, 2012 (JP) ................. 2012-034925

(51) Int. Cl.
H05G 1/02 (2006.01)
A61B 6/14 (2006.01)
(Continued)

(52) U.S. Cl.
CPC ............. *A61B 6/14* (2013.01); *A61B 6/027* (2013.01); *A61B 6/032* (2013.01); *A61B 6/4429* (2013.01);
(Continued)

(58) Field of Classification Search
CPC ............. A61B 6/06; A61B 6/14; A61B 6/027; A61B 6/032; A61B 6/56; A61B 6/563; A61B 6/587; A61B 6/588; A61B 6/589; A61B 6/4429; A61B 6/4476
(Continued)

(56) References Cited

U.S. PATENT DOCUMENTS 6,118,842 A 9/2000 Arai et al.
6,173,035 B1 * 1/2001 Tachibana ................ A61B 6/14
378/39

(Continued)

FOREIGN PATENT DOCUMENTS

EP 0 904 734 A2 3/1999
JP 10-225455 A 8/1998
(Continued)

OTHER PUBLICATIONS

Extended European Search Report for corresponding PCTJP2013/052946 application dated Oct. 12, 2015 (6 pages).
(Continued)

Primary Examiner — Courtney Thomas
(74) Attorney, Agent, or Firm — Capitol City TechLaw, PLLC; Samuel P. Burkholder

(57) ABSTRACT

Radiographic X-ray equipment includes a revolution driving device that causes an X-ray irradiating member and an X-ray imaging member to perform a revolving movement around a subject with a revolution center line as the center, and a main body control unit that controls the revolution driving device, a secondary driving device controlled by the main body control unit to cause the X-ray imaging member to perform a local movement different from the revolving movement, with a movement width in a predetermined direction, a storing means that stores electric power for the X-ray imaging member, and a supplying means that supplies
(Continued)

electric power to the storing means. The X-ray imaging member and the storing means are connected to each other, and the secondary driving device causes the storing means and the X-ray imaging member to perform the local movement as a unit without moving relative to each other.

6 Claims, 13 Drawing Sheets

(51) Int. Cl.
*A61B 6/02* (2006.01)
*A61B 6/03* (2006.01)
*A61B 6/00* (2006.01)
*A61B 6/06* (2006.01)

(52) U.S. Cl.
CPC ............... *A61B 6/4476* (2013.01); *A61B 6/56* (2013.01); *A61B 6/563* (2013.01); *A61B 6/587* (2013.01); *A61B 6/588* (2013.01); *A61B 6/06* (2013.01); *A61B 6/589* (2013.01)

(58) Field of Classification Search
USPC ............................... 378/38–40, 62, 101–103
See application file for complete search history.

(56) References Cited

U.S. PATENT DOCUMENTS

| | | |
|---|---|---|
| 7,250,608 B2 | 7/2007 | Ozeki |
| 8,798,236 B2 | 8/2014 | Ohta et al. |
| 2006/0202127 A1 | 9/2006 | Ozeki |
| 2011/0188633 A1 | 8/2011 | Ohta et al. |
| 2013/0136226 A1 | 5/2013 | Tomoe et al. |

FOREIGN PATENT DOCUMENTS

| | | |
|---|---|---|
| JP | 11-104128 A | 4/1999 |
| JP | 2003-175031 A | 6/2003 |
| JP | 2008-134057 A | 6/2008 |
| JP | 2011-194216 A | 10/2011 |
| WO | 2012020467 A1 | 2/2012 |

OTHER PUBLICATIONS

International Search Report for corresponding PCTJP2013/052946 application dated Mar. 5, 2013 (2 pages).

* cited by examiner

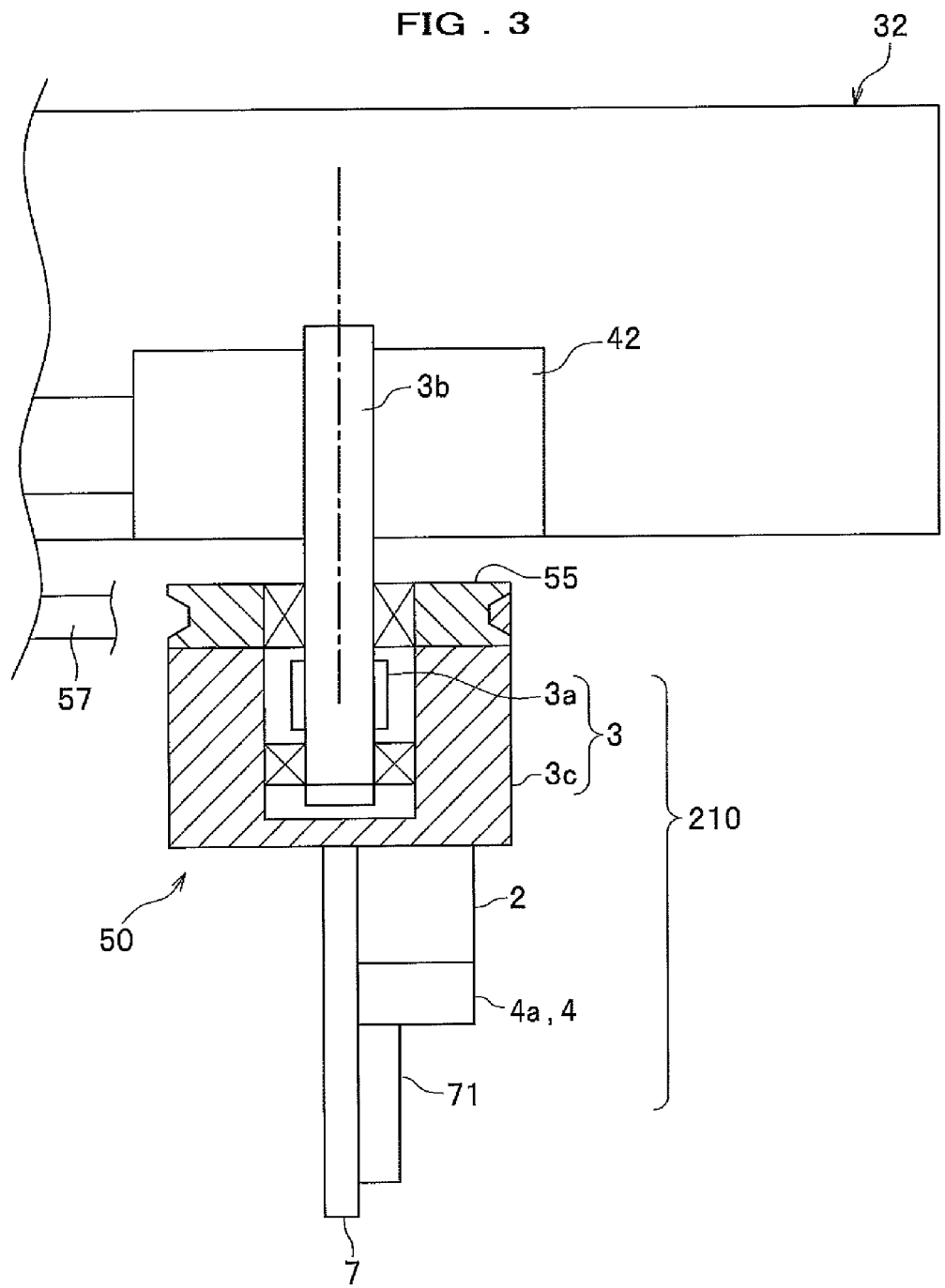

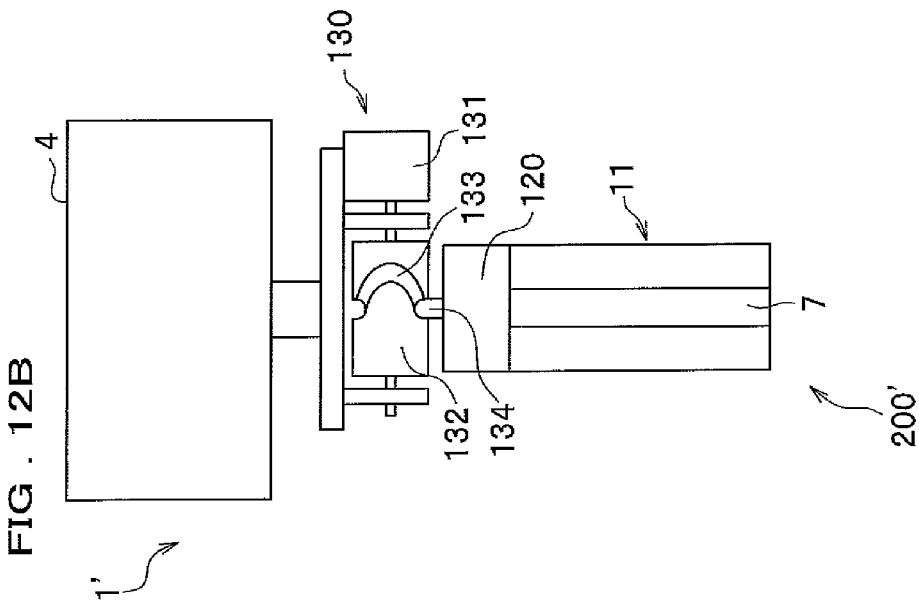
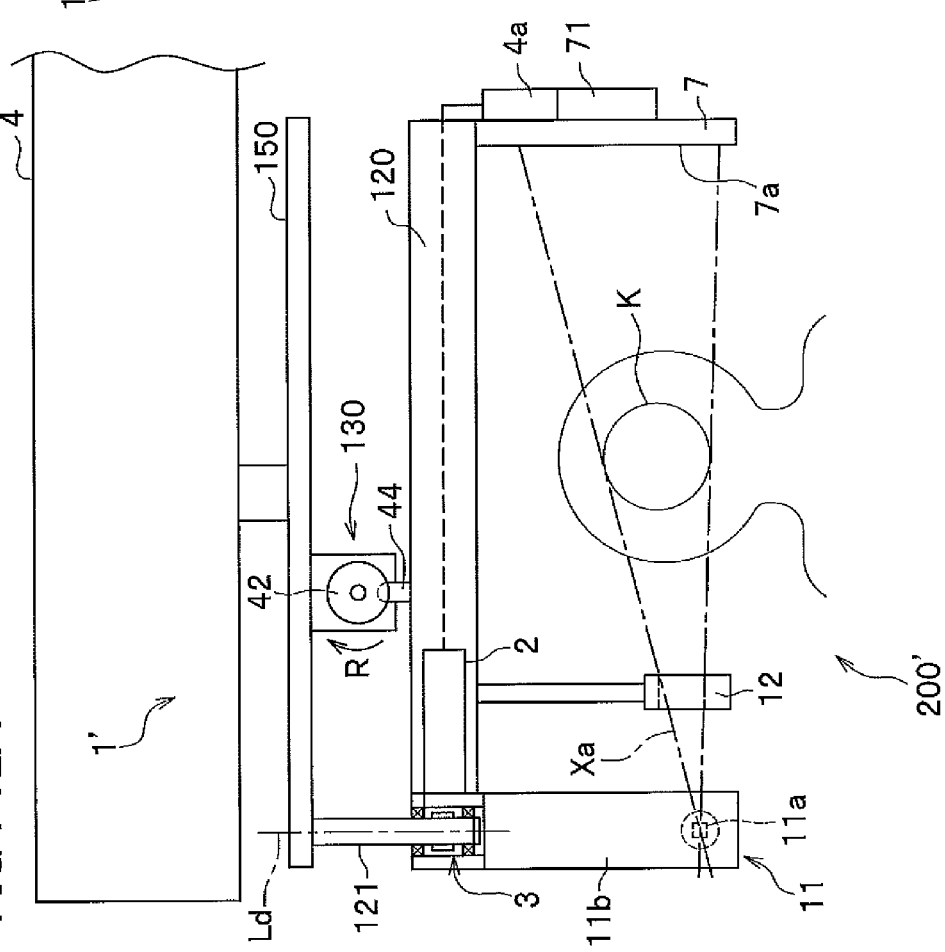

RADIOGRAPHIC X-RAY EQUIPMENT

TECHNICAL FIELD

The present invention relates to radiographic X-ray equipment that generates an X-ray image of a subject based on image data acquired by an X-ray imaging member that receives an X-ray flux which is radiated from an X-ray irradiating member and transmitted through the subject. The radiographic X-ray equipment is used, for example, in dental examination.

BACKGROUND ART

For example, there is known radiographic X-ray equipment for dental examination, which is provided with an X-ray irradiating member that irradiates a subject with an X-ray flux, an X-ray imaging member with an acceptance surface provided for receiving the X-ray flux transmitted through the subject, and a driving device that causes the X-ray irradiating member and the X-ray imaging member to perform a revolving movement around the subject, and which can perform CT imaging and panoramic radiography (for example, see Patent Literatures 1, 2).

CITATION LIST

Patent Literature

Patent Literature 1: Japanese Patent Application Publication No. H10-225455
Patent Literature 2: Japanese Patent Application Publication No. 2003-175031 (FIG. 14)

SUMMARY OF INVENTION

Technical Problem

When radiographic X-ray equipment employs an X-ray imaging member used in CT imaging in order to enable CT imaging and panoramic radiography, the radiographic X-ray equipment provided with such an X-ray imaging member becomes expensive because an X-ray imaging member for CT imaging has a broad acceptance surface and thus is expensive.

Moreover, in the case of causing an X-ray imaging member to perform a local movement at high speed in order to acquire a broad acceptance surface, there are problems that bad connection of a cable via which supply of power to drive the X-ray imaging member and transmitting and receiving of signals are performed, and/or noises are generated.

The present invention has been made in view of these circumstances and firstly makes it an object, in radiographic X-ray equipment provided with an X-ray irradiating member and an X-ray imaging member, to cause the X-ray imaging member to perform a local movement different from a revolving movement to thereby acquire a broad acceptance surface, and to accomplish cost reduction of the radiographic X-ray equipment.

The present invention secondly makes it an object to suppress generation of bad connection of a cable and/or noises in the case of causing the X-ray imaging member to perform a local movement different from a revolving movement, to thereby improve detection accuracy and increase reliability and durability.

Solution to Problem

The invention provides radiographic X-ray equipment including an X-ray irradiating member that irradiates a subject with an X-ray flux, an X-ray imaging member with an acceptance surface provided for receiving the X-ray flux transmitted through the subject, a revolution driving device that causes the X-ray irradiating member and the X-ray imaging member to perform a revolving movement around the subject with a revolution center line as the center, and a main body control unit that controls the revolution driving device, the radiographic X-ray equipment including: a secondary driving device that is controlled by the main body control unit to cause the X-ray imaging member to perform a local movement different from the revolving movement, with a movement width in a predetermined direction; an electricity storing means that stores electric power to be supplied to the X-ray imaging member; and an electric power supplying means that supplies electric power to the electricity storing means, the X-ray imaging member and the electricity storing means being connected to each other, and the secondary driving device causing the electricity storing means and the X-ray imaging member to perform the local movement as a unit without moving relative to each other.

According to this configuration, since the width of the acceptance surface of the X-ray imaging member in the predetermined direction is small as compared to the movement width in the predetermined direction of the X-ray imaging member that is driven by the secondary driving device to perform the local movement, an inexpensive X-ray imaging member can be used as compared to an X-ray imaging member having an acceptance surface of a size corresponding to the movement width, thereby enabling a reduction in cost of the radiographic X-ray equipment.

Since the electricity storing means that stores electric power to be supplied to the X-ray imaging member is provided, it is possible to stably supply the electric power from the electricity storing means to the X-ray imaging member. Moreover, since the electricity storing means and the X-ray imaging member are caused to perform the local movement as a unit without moving relative to each other, no relative movement is generated at all between the X-ray imaging member and the electricity storing means, thereby making it possible to certainly prevent disconnection and/or bad connection of wires.

Thus, the present invention makes it possible, while causing the X-ray imaging member to perform the local movement different from the revolving movement to thereby acquire a broad acceptance surface and accomplish cost reduction of the radiographic X-ray equipment, to suppress generation of bad connection of a cable and/or noises in the case of causing the X-ray imaging member to perform the local movement different from the revolving movement, and to accomplish improvement in reliability and durability.

The invention provides the radiographic X-ray equipment as set forth above, wherein the electric power supplying means includes a wireless power transmission device that wirelessly transmits electric power to the electricity storing means. According to this configuration, since electric power is wirelessly transmitted to the electricity storing means and thus there is no wire between the electric power supplying means and the electricity storing means, it is possible to certainly suppress generation of bad connection of a cable and/or noises in the case of causing the X-ray imaging member to perform the local movement different from the revolving movement, and to accomplish improvement in high reliability and durability.

The invention provides the radiographic X-ray equipment as described above, wherein the electric power supplying means includes an electricity generating means that is connected by wire with the electricity storing means, and the electricity generating means is provided at a position to perform a local movement as a unit without moving relative to the electricity storing means and the X-ray imaging member.

According to this configuration, since the electricity generating means, the electricity storing means and the X-ray imaging member are caused to perform the local movement as a unit without moving relative to one another, it is possible to certainly prevent disconnection and/or bad connection of wires between the X-ray imaging member and the electricity storing means.

The invention further provides in some embodiments the above-described radiographic X-ray equipment, wherein the local movement is a rotational movement, and the electricity generating means utilizes a rotational force by the rotational movement to generate electricity. According to this configuration, since the rotational movement of the radiographic X-ray equipment is utilized to generate electricity and the electricity can be generated near the X-ray imaging member, it becomes easy to cause the electricity generating means, the electricity storing means and the X-ray imaging member to perform the local movement as a unit without moving relative to one another. Consequently, it is possible to certainly prevent disconnection and/or bad connection of wires between the X-ray imaging member and the electricity storing means.

Moreover, since the local movement of the X-ray imaging member is a rotational movement, it is possible to make unnecessary a temporary stop which would be generated when the X-ray imaging member is subjected to an arc movement or a linear movement, and/or an operation for restarting after the temporary stop. As a result, it is possible to decrease acceleration and deceleration which act on the X-ray imaging member, and accordingly to reduce inertial force due to the acceleration and deceleration. Consequently, it is possible to reduce vibration of the X-ray imaging member due to the inertial force and to improve durability of the X-ray imaging member. Furthermore, it is possible to suppress a decrease in speed due to a temporary stop of the X-ray imaging member for the duration of the start to the end of the X-ray imaging, and/or an operation for restarting, and accordingly to improve an efficiency in X-ray imaging work by speed-up of the driven member.

The invention also includes radiographic X-ray equipment, wherein the electricity generating means includes a photoelectric conversion means that converts light energy into electrical energy. According to this configuration, since the photoelectric conversion means is adopted as the electricity generating means, it is possible to drive the X-ray imaging member even in the case of being unable to utilize a rotational movement to generate electricity, or in the case of running short of electric power generated by a rotational movement.

In some embodiments of the present invention, the radiographic X-ray equipment described above further includes: a data detection circuit that detects an X-ray flux received by the X-ray imaging member, as image data; an image processing device that is provided in the main body control unit and processes the image data detected by the data detection circuit; and a transmitting and receiving device that wirelessly communicates data between the image processing device and the data detection circuit.

According to this configuration, since transmitting and receiving between the data detection circuit and the main body control unit are wirelessly carried out and, in addition to transmission of electric power by wireless, transmitting and receiving of data are also wirelessly carried out, it is possible to comprehensively suppress generation of bad connection of a cable and/or noises and to ensure high reliability and durability.

Advantageous Effects of Invention

The radiographic X-ray equipment provided with the X-ray irradiating member and the X-ray imaging member, according to the present invention, firstly makes it possible, in radiographic X-ray equipment provided with an X-ray irradiating member and an X-ray imaging member, to cause the X-ray imaging member to perform a local movement different from a revolving movement to thereby acquire a broad acceptance surface, and to accomplish cost reduction of the radiographic X-ray equipment.

The radiographic X-ray equipment provided with the X-ray irradiating member and the X-ray imaging member, according to the present invention, secondly makes it possible to suppress generation of bad connection of a cable and/or noises in the case of causing the X-ray imaging member to perform a local movement different from a revolving movement, to thereby improve detection accuracy and increase reliability and durability.

BRIEF DESCRIPTION OF DRAWINGS

FIG. 2A is a side view inclusive of a cross-sectional view and FIG. 2B is a bottom plan view showing the main parts in FIG. 2A.

FIG. 3 is a cross-sectional view showing a configuration of a sensor unit around the X-ray imaging member.

FIG. 6A is a perspective view showing an example which adopts a photoelectric conversion means, and FIG. 6B is a block diagram showing an example which adopts wireless power transmission.

FIG. 7A is a top plan view and FIG. 7B is a front view.

FIGS. 12A and 12B are enlarged views showing main parts in the third embodiment of the present invention, where FIG. 12A is a front view and FIG. 12B is a side view.

FIG. 13A shows a position at one end in the arc movement range of the arc movement means, FIG. 13B shows a position at the center therein, and FIG. 13C shows a position at another end therein.

DESCRIPTION OF EMBODIMENTS

Hereinafter, a first embodiment of the present invention will be described with reference to FIGS. 1 to 8.

Figure 1:
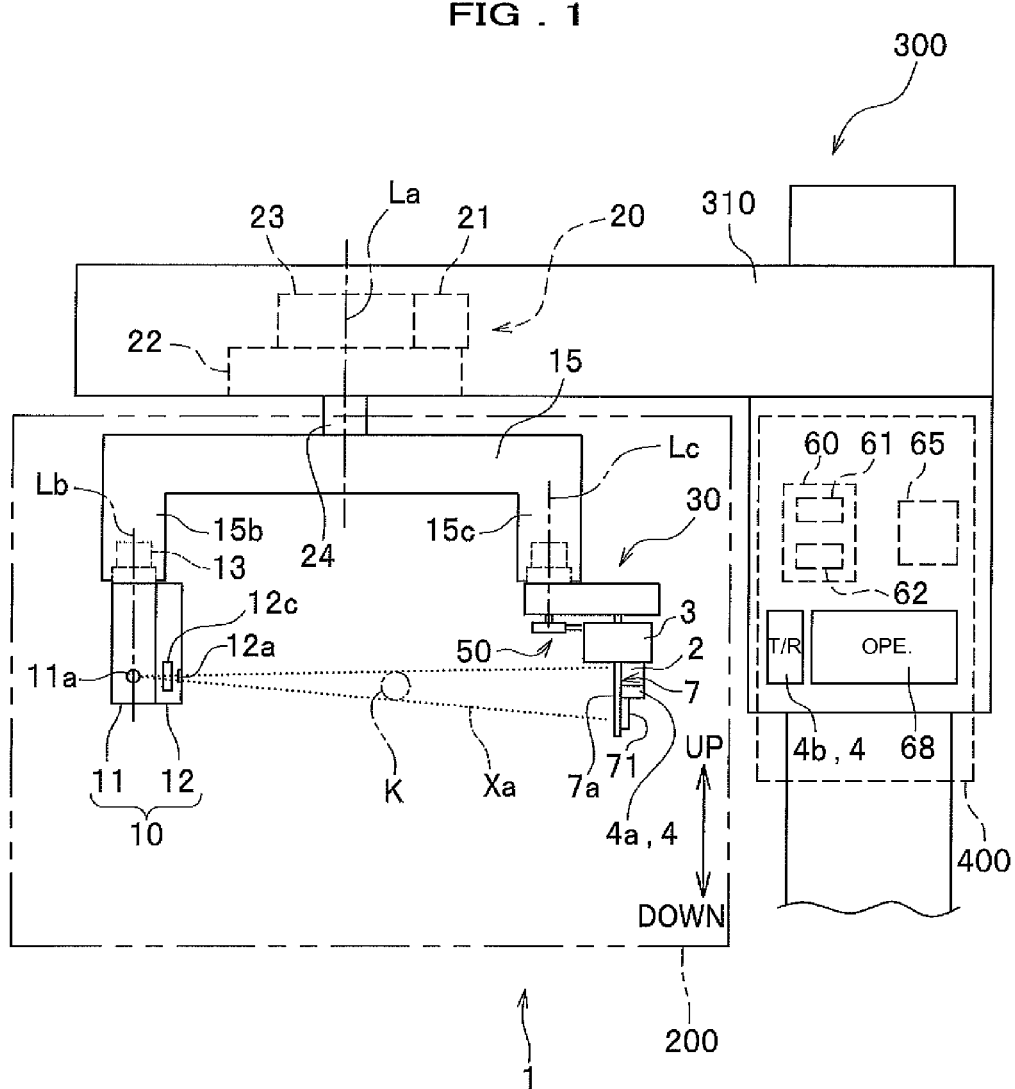
FIG. 1 is a front view in a schematic view showing main parts in radiographic X-ray equipment according to a first embodiment of the present invention.

Referring to FIG. 1, radiographic X-ray equipment 1 according to the first embodiment is used, with a target as human, in dental examination as medical care.

The radiographic X-ray equipment 1 is provided with a main body apparatus 200, a supporting apparatus 300 having a frame 310 which supports the main body apparatus 200, a main body control unit 400 provided on the supporting apparatus 300, and a transmitting and receiving device 4 that communicates with the main body apparatus 200 and the main body control unit 400.

The supporting apparatus 300 is set up on a structure (not shown) in which the radiographic X-ray equipment 1 is placed, and the frame 310 is adapted to support the main body apparatus 200 position-adjustably in an up-and-down direction in the supporting apparatus 300. As another example, the main body apparatus 200 may be provided with a mechanism for making itself position-adjustable relative to the frame 310 in the up-and-down direction.

<Main body apparatus>

The main body apparatus 200 is provided with an X-ray irradiating member 10 that irradiates a subject K (for example, dental arch, cephalic part including the dental arch) with an X-ray flux Xa, an X-ray imaging member (X-RAY I.M.) 7 with an acceptance surface 7a provided for receiving the X-ray flux Xa transmitted through the subject K, an arm 15 as a supporting member that supports the X-ray irradiating member 10 and the X-ray imaging member 7 which are arranged across the subject K in the irradiation direction of the X-ray flux Xa from the X-ray irradiating member 10, a revolution driving device 20 that revolves the arm 15 to cause the X-ray irradiating member 10 and the X-ray imaging member 7 to perform a revolving movement around the subject K with a revolution center line La as the center, an imaging-side driving device 30 and a rotation mechanism 50 that cause the X-ray imaging member 7 as a driven member to perform a local rotational movement which is a rotational movement as a local movement different from the revolving movement, an electricity storing means (E.S.) 2 that stores electric power required for driving the X-ray imaging member 7, a generator 3 which is an electric power supplying means that supplies electric power to the electricity storing means 2, and a data detection circuit 71 that detects image data acquired by the X-ray imaging member 7.

Here, the revolution driving device 20, a secondary driving device constituted by the imaging-side driving device 30 and the rotation mechanism 50 in this embodiment, and a driving member 13 as described later, constitute a driving device of the radiographic X-ray equipment 1.

The transmitting and receiving device 4 is provided with a sensor unit transmitting and receiving device (T/R) 4a provided in the main body apparatus 200, and a main body transmitting and receiving device (T/R) 4b provided in the main body control unit 400, and is adapted to wirelessly communicate data between the main body control unit 400 (image processing device) and the data detection circuit 71.

Figure 5:
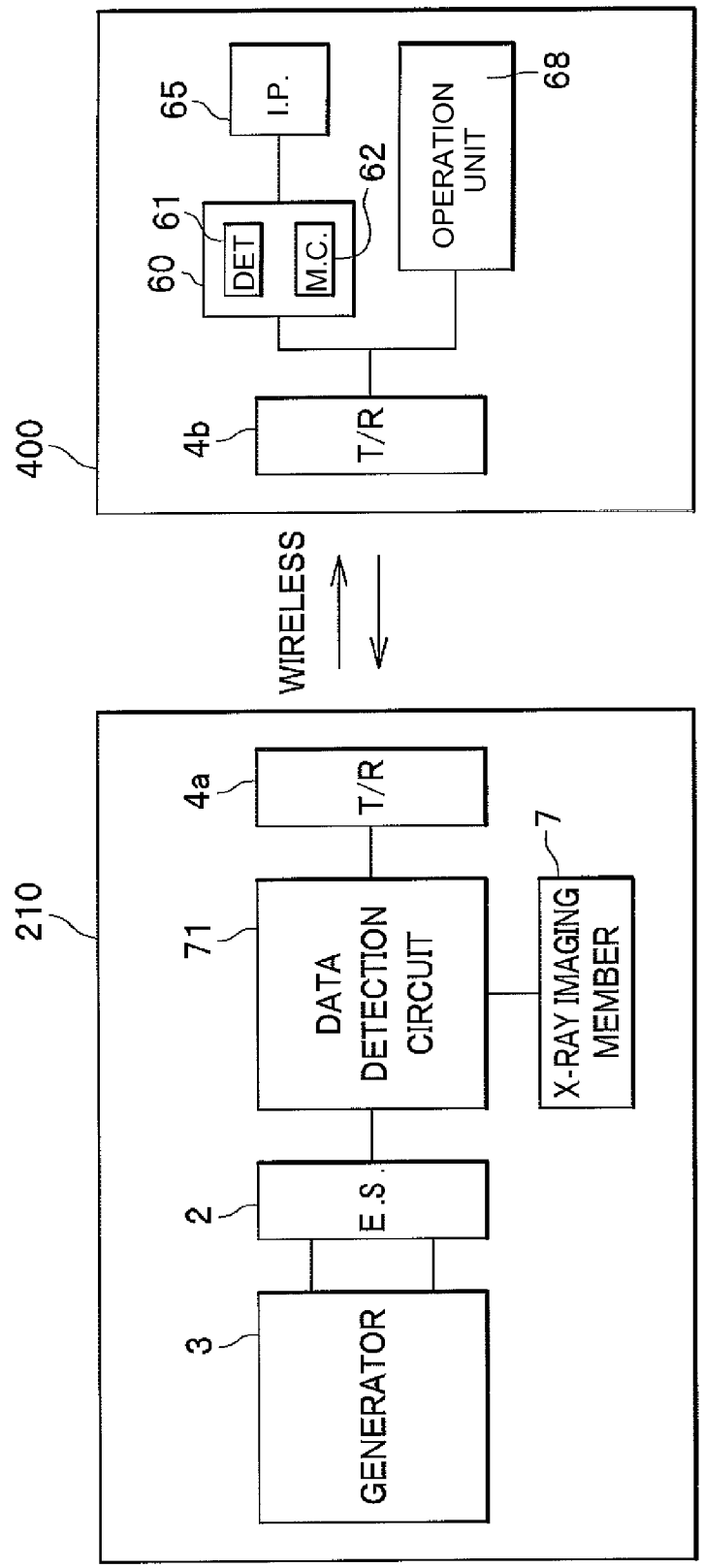
FIG. 5 is a block diagram showing a relationship between the sensor unit and a main body control unit.
Figure 6A:
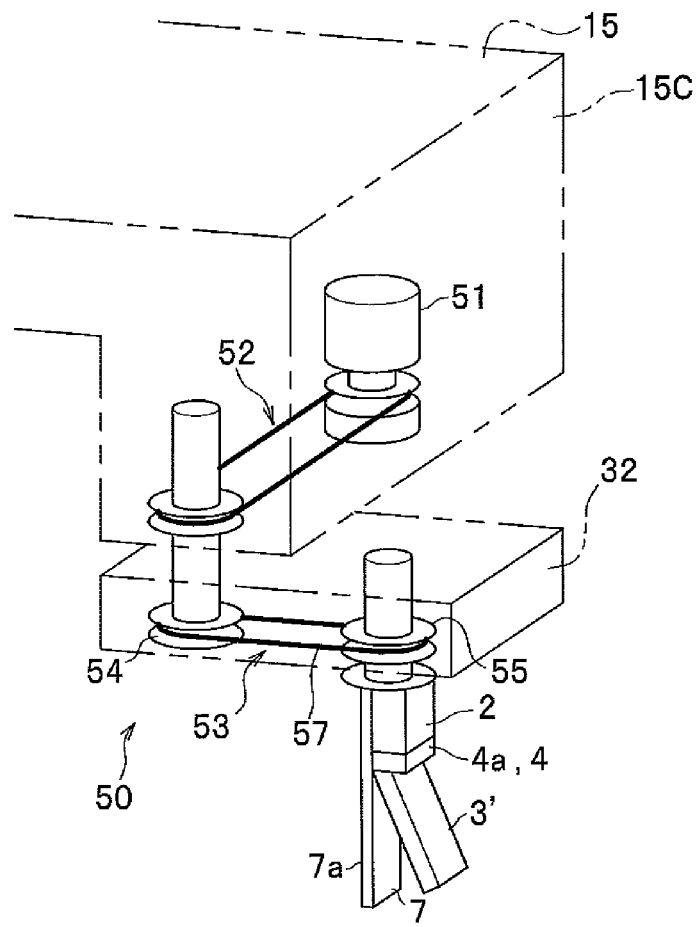
FIGS. 6A and 6B are views illustrating a modified example of the first embodiment of the present invention, where
Figure 6B:
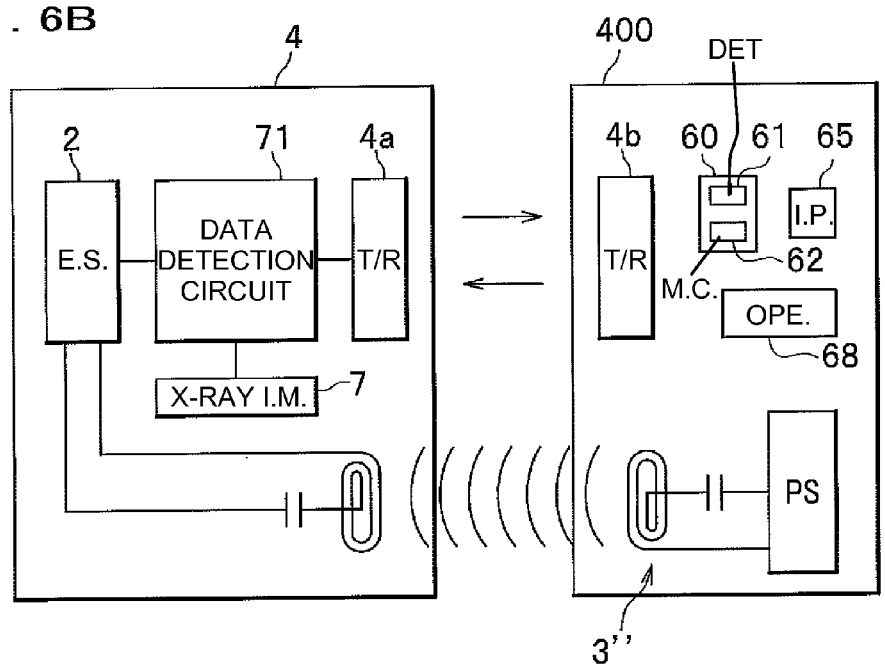

In the main body apparatus 200, for convenience, the unit that includes the X-ray imaging member 7, the electricity storing means 2, the generator 3 which is an electric power supplying means, the data detection circuit 71 and the sensor unit transmitting and receiving device 4a, is referred to as a sensor unit 210 (see FIG.5).

<X-Ray Irradiating Member>

The X-ray irradiating member 10 which is supported by an irradiating-side supporting portion 15b of the arm 15 includes an X-ray radiating member 11 having an X-ray source 11a that radiates X-rays, and a slit member 12 as an X-ray flux forming member that forms X-ray flux from the X-ray source 11a into a slit-shaped X-ray flux Xa. The slit member 12 includes a radiation unit which is constituted by a collimator 12c that defines the irradiation range and irradiation direction of the X-ray flux Xa, and a slit 12a that allows the X-ray flux formed by the collimator 12c to pass therethrough. Accordingly, the collimator 12c and the slit 12a from which the X-ray flux Xa is radiated, and the acceptance surface 7a, are located at positions across the subject K in the irradiation direction of the X-ray flux Xa in the arm 15 (see also FIGS. 7A and 7B).

The X-ray radiating member 11 and the slit member 12 are provided on the arm 15 and driven by the driving member 13 that is controlled by the main body control unit 400, so as to perform a rotational movement or a linear movement to be movable relative to the arm 15.

More specifically, the driving member 13 causes the X-ray source 11a, the collimator 12c and the slit 12a to move to follow the acceptance surface 7a which performs the local rotational movement, while keeping the state in which the X-ray source 11a, the collimator 12c, the slit 12a, the subject K and the acceptance surface 7a are positioned in alignment with one another. In the present embodiment, the driving member 13 causes the X-ray source 11a, the collimator 12c and the slit 12a to perform the rotational movement with a radiation center line Lb which passes through the X-ray source 11a and is parallel with the revolution center line La, as the center, thereby causing the X-ray source 11a, the collimator 12c and the slit 12a to move in the form of an arc or in the circumferential direction. As another example, the driving member 13 may cause the X-ray source 11a, the collimator 12c and the slit 12a to perform the linear movement.

<X-Ray Imaging Member>

The X-ray imaging member 7 having the acceptance surface 7a is a two-dimensional X-ray imaging member that is constituted by an image sensor such as CMOS sensor, CdTe sensor or CCD sensor, and is a CMOS sensor as an example in the embodiment described below.

Figure 2A:
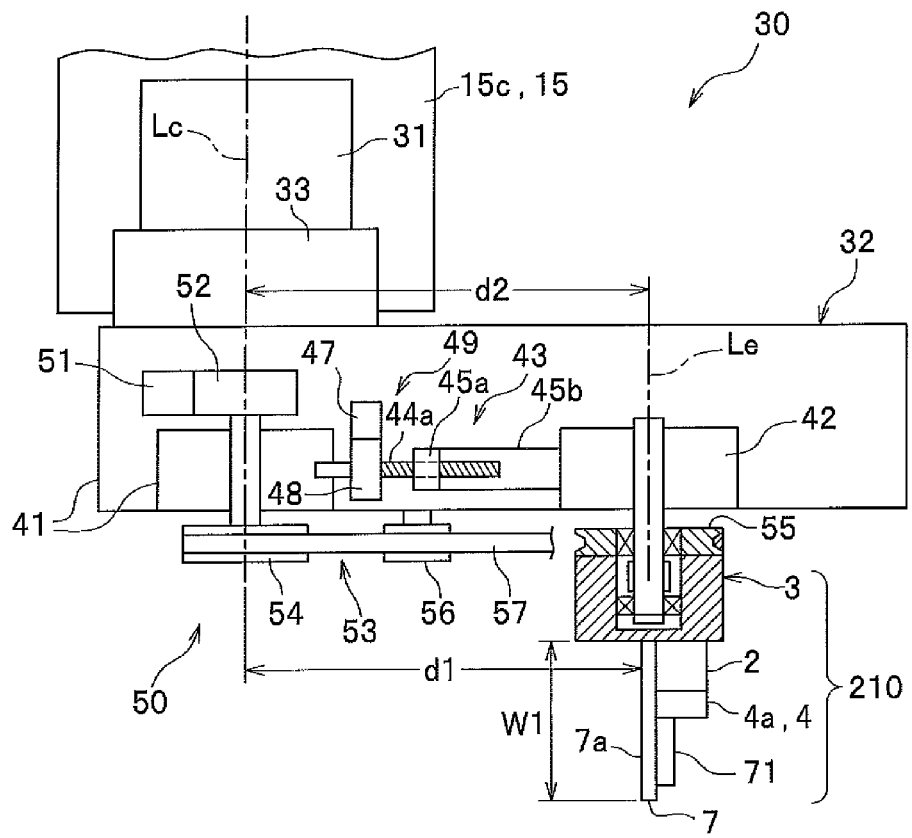
FIGS. 2A and 2B are schematic views showing main parts near an X-ray imaging member of the radiographic X-ray equipment in FIG. 1, where
Figure 2B:
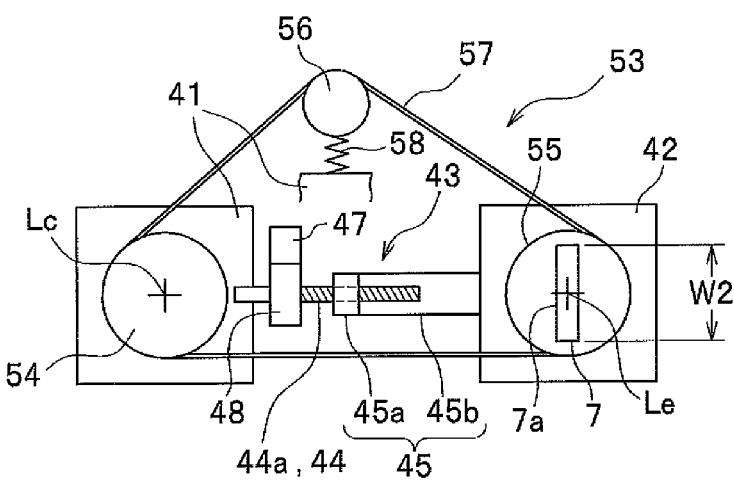

As shown in FIGS. 2A and 2B, the acceptance surface 7a has an elongated shape in which a width W1 in its longitudinal direction is greater than a width W2 in the direction perpendicular to the longitudinal direction. With the X-ray imaging member 7 being supported by the arm 15, the longitudinal direction of the acceptance surface 7a is a direction nearly parallel with the revolution center line La in the first embodiment.

Note that in the description and the claims, the expression "nearly" includes the case where there is no modifying word "nearly", and also means the scope with which there is no significant difference with respect to the operation and advantageous effects as compared to the case where there is no modifying word "nearly", although not strictly identical to the case where there is no modifying word "nearly".

Referring to FIG. 1, the revolution driving device 20 is provided with a servo motor 21 as an actuator for revolution that is provided in the frame 310 and rotates the arm 15, an XY table 22 as a two-dimensional driving device that is rotationally driven by the servo motor 21 and moves the arm 15 on the horizontal plane as a two-dimensional plane which is perpendicular to the revolution center line La, a transmission mechanism 23 that includes a speed reduction mechanism and transmits driving force of the servo motor 21 to the XY table 22, and a connecting shaft 24 as a connecting part that connects the servo motor 21 to the arm 15 via the transmission mechanism 23 and the XY table 22. The arm 15 is rotationally driven by the servo motor 21 via the transmission mechanism 23, the XY table 22 and the connecting shaft 24, so as to rotate with the revolution center line La as the center to thereby revolve the X-ray irradiating member 10 and the X-ray imaging member 7.

Here, the "revolution" includes the case of making one or more revolutions and the case of making less than one revolution, with the revolution center line La as the center. Moreover, the speed reduction mechanism included in the transmission mechanism 23, speed reduction mechanisms included in transmission mechanisms 33, 52 as described later, and a speed reduction mechanism 48 (see FIGS. 2A and 2B) are constituted by, for example, a worm gear mechanism.

<Imaging-Side Driving Device>

Referring to FIG. 1, FIGS. 2A and 2B, the imaging-side driving device 30 provided on the arm 15 is provided with a servo motor 31 which is an imaging-side actuator, a holding member 32 that holds the X-ray imaging member 7, and a transmission mechanism 33 that includes a speed reduction mechanism and transmits driving force of the servo motor 31 to the holding member 32. The X-ray imaging member 7 and the acceptance surface 7a are rotationally driven by the servomotor 31 via the transmission mechanism 33 and the holding member 32, so as to perform a local rotational movement (see FIGS. 7A and 7B) with a rotation centerline Lc which is a straight line other than the revolution center line La, as the center.

Figure 7A:
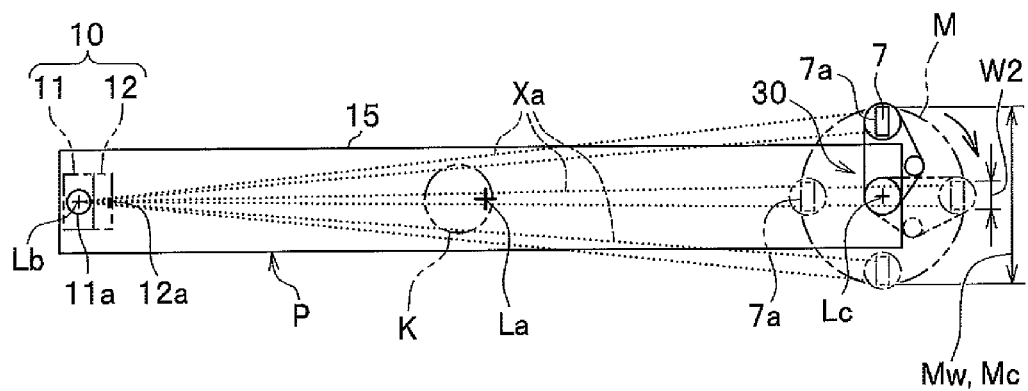
FIGS. 7A and 7B are schematic views for explaining a local rotational movement of the X-ray imaging member when an arm of the radiographic X-ray equipment in FIG. 1 occupies one revolution position, where
Figure 7B:
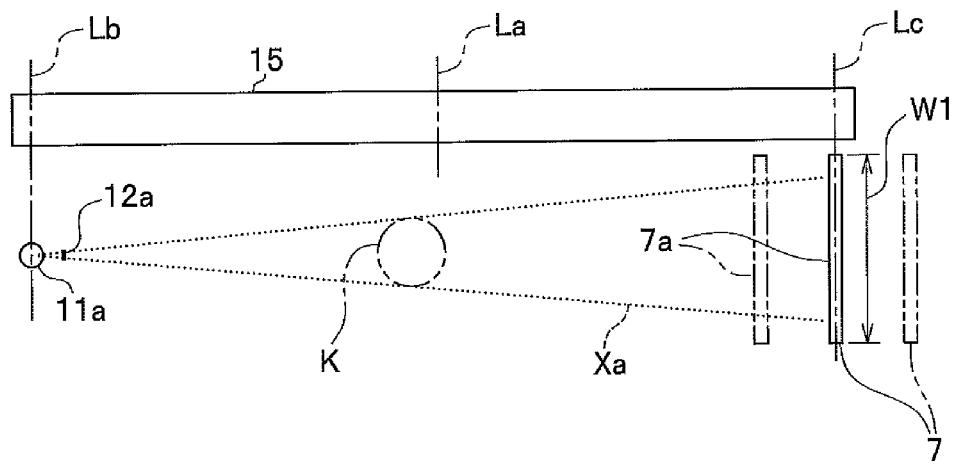

Referring to FIGS. 7A and 7B additionally, the local rotational movement is defined based on a distance d1 between the rotation center line Lc and the X-ray imaging member 7 in the radial direction with the rotation center line Lc as the center, or a predetermined distance d2 as described later, and becomes a movement within the range of a movement width Mw in a predetermined direction when the predetermined direction is defined by a circumferential direction with the revolution center line La (see FIG. 1) as the center. The width W2, which is a width of the acceptance surface 7a in the circumferential direction which is the predetermined direction, is smaller than the movement width Mw. Also, in the local rotational movement, the acceptance surface 7a rotates with its longitudinal direction being nearly parallel with the revolution centerline La, accordingly with an elongated state in the revolution center line direction (also in the up-and-down direction in this embodiment) which is a direction parallel with the revolution center line La.

Moreover, when the X-ray imaging member 7 makes one revolution around the rotation center line Lc relative to the arm 15, the rotation center line Lc is arranged so that the subject K is positioned at all times between the slit 12a of the X-ray irradiating member 10 and the acceptance surface 7a of the X-ray imaging member 7 in the irradiation direction of the X-ray flux Xa.

Referring to FIGS. 2A and 2B, the holding member 32 is rotatably supported by an imaging-side supporting portion 15c of the arm 15 with the rotation center line Lc as the center, so as to rotate with the rotation center line Lc as the center. Moreover, the X-ray imaging member 7 is rotatably supported by the holding member 32 with a rotation center line Le which is a secondary rotation center line positioned at the predetermined distance d2 from the rotation center line Lc, as the center.

More specifically, the holding member 32 is provided with a first base 41 that is rotationally driven by the servo motor 31 via the transmission mechanism 33, a second base 42 that rotatably supports the X-ray imaging member 7 with the rotation center line Le as the center and is supported on the first base 41 movably in the radial direction of the rotation center line Lc, a connecting member 43 that connects the first base 41 with the second base 42 and is extendable in the radial direction of the rotation center line Lc, a servo motor 47 as an actuator for distance adjustment that elongates and contracts the connecting member 43 in the radial direction of the rotation center line Lc, and the rotation mechanism 50 that rotationally drives the X-ray imaging member 7 and the acceptance surface 7a with the rotation center line Le as the center. The connecting member 43 defines the predetermined distance d2 between the rotation center line Lc and the rotation center line Le.

Here, in the present embodiment, the "local movement" is configured inclusive of the local rotational movement (rotation) by the rotation mechanism 50, and the secondary driving device is configured inclusive of the local rotational movement by the imaging-side driving device 30 and the local rotational movement (rotation) by the rotation mechanism 50.

The rotation mechanism 50 is provided with a servo motor 51 as an actuator for rotation that is rotatably supported by the first base 41, a transmission mechanism 52 that includes a speed reduction mechanism, and a power transmission mechanism 53 that is rotationally driven by the servo motor 51 via the transmission mechanism 52, so as to rotate the X-ray imaging member 7.

Moreover, the power transmission mechanism 53 is provided with a driving pulley 54 as a driving part, a driven pulley 55 as a driven part which is rotatably supported by the second base 42 and to which the X-ray imaging member 7 is provided fixedly, an idle pulley 56 which is rotatably supported by the first base 41, and a belt 57 as an endless power transmission belt which is stretched over these pulleys 54, 55 and 56. The idle pulley 56 is urged by a spring 58 as an urging member, to function as a tensioner which gives tension to the belt 57.

A rotation center line of the driving pulley 54 is coaxial with the rotation center line Lc, but may be parallel with the rotation center line Lc in another example. Moreover, a rotation center line of the driven pulley 55 is the rotation center line Le.

The connecting member 43 includes a first connecting part 44 which is provided on the first base 41, and a second connecting part 45 which is provided on the second base 42 and is movable linearly relative to the first connecting part 44 in the radial direction of the rotation center line Lc. In the present embodiment, the first connecting part 44 is comprised of a screw rod 44a which is rotatably supported by the first base 41 and is rotationally driven by the servo motor 47. Also, the second connecting part 45 is comprised of a female screw part 45a into which the screw rod 44a is screwed, and of a connecting rod 45b which rotatably supports the female screw part 45a serving as a connection part for the screw rod 44a and is fixed on the second base 42 to move together with the female screw part 45a and the second base 42 in the radial direction.

When the servomotor 47 rotationally drives the screw rod 44a via a speed reduction mechanism 48 as a transmission mechanism, the second connecting part 45 which is connected via the female screw part 45a to the screw rod 44a rotates and moves along the first connecting part 44 in the radial direction of the rotation center line Lc, thereby changing the distance d1 and the predetermined distance d2.

Accordingly, the connecting member 43, the servomotor 47 and the speed reduction mechanism 48 constitute a distance adjusting mechanism 49 which can change the distance d1 and the predetermined distance d2 between the rotation center line Lc and the acceptance surface 7a of the X-ray imaging member 7.

Therefore, it is possible to change the movement width Mw (see FIG. 7A) by changing the length of the connecting member 43 with actuation of the servo motor 47 to change the distance d1 and the predetermined distance d2, and it is possible to change radiographic area on the acceptance surface 7a which performs the local rotational movement without changing a revolution position P (see FIG. 7A, FIGS. 8A and 8B) of the arm 15. For example, by making the connecting member 43 longer than the state shown in FIGS. 2A and 2B, the movement width Mw and the radiographic area on the acceptance surface 7a become larger than the movement width Mw and the radiographic area in the case shown in FIG. 7A.

Note, in the first embodiment, the length of the connecting member 43 is constant at an arbitrary position of the X-ray imaging member 7 which performs the local rotational movement, and at an arbitrary revolution position P of the arm 15 which performs the revolving movement.

Referring to FIGS. 7A and 7B additionally, the servo motor 51 directs the acceptance surface 7a toward the slit 12a across the subject K in the radiation direction so that the acceptance surface 7a can receive the X-ray flux Xa transmitted through the subject K at all times. To this end, the servo motor 51 is controlled by a motion control device 60 to thereby rotationally drive the driving pulley 54 and further rotationally drive the driven pulley 55, in synchronization with the local rotational movement of the X-ray imaging member 7. Rotational speeds of the driving pulley 54 and the driven pulley 55 are set to be equal to each other in this embodiment, but may be set to be different rotational speeds.

The acceptance surface 7a driven by the servo motor 51 rotates at an arbitrary position on a movement path M (FIG. 7A shows a schematic outer circumference of the movement path M) by the local rotational movement so that it becomes parallel with a plane perpendicular to a line which passes through the revolution center line La and the rotation center line Lc when viewed from the revolution center line direction. As another example, the acceptance surface 7a may be rotated to be directed toward the radiation center line Lb at all times.

Moreover, as still another example, a configuration may be adopted in which the rotation mechanism 50 is provided, in place of the servo motor 51, with a cooperative mechanism (for example, constituted by a gear mechanism) that transmits rotation of the servo motor 31 to the driving pulley 54, to thereby cause the servo motor 31 to rotationally drive the driving pulley 54 via the cooperative mechanism, in synchronization with the local rotational movement of the X-ray imaging member 7. This configuration makes it possible to avoid twist of an electric wire of the servo motor 51 by mechanically transmitting the rotation of the servo motor 31, without using the servo motor 51 to which electric power must be supplied.

Accordingly, as shown in FIGS. 7A and 7B, the arm 15 driven by the revolution driving device 20 (see FIG. 1) rotates and in the state in which the X-ray irradiating member 10 and the X-ray imaging member 7 occupy the revolution position P, the X-ray imaging member 7 rotates with the rotation center line Lc as the center (FIG. 7A shows the positions at intervals of nearly 90°). Moreover, depending on a rotational position of the acceptance surface 7a, the X-ray irradiating member 10 is rotationally driven by the driving member 13 (see FIG. 1) in the circumferential direction with the revolution center line La as the center, to move to the position at which the slit 12a and the acceptance surface 7a face each other across the subject K in the irradiation direction of the X-ray flux Xa.

<Electricity Storing Means>

The electricity storing means 2 is a charging apparatus which is provided on the generator 3 as a unit, stores therein electric power generated by the generator 3, and supplies the electric power to the X-ray imaging member 7, the data detection circuit 71 and the sensor unit transmitting and receiving device 4a which are provided in the sensor unit 210 (see FIG. 5). As the charging apparatus, a rechargeable storage cell can be appropriately adopted, such as a rechargeable lithium-ion battery (lithium-ion storage cell), an electric double layer capacitor, a nickel hydride battery, a nickel-cadmium (NiCd) battery or a lead battery. Since the electric double layer capacitor and the lithium-ion storage cell excel especially in the amount of energy per volume, they make it possible to accomplish weight saving and downsizing.

<Electric Power Supplying Means>

The generator 3 which is an electric power supplying means is a device that converts rotational energy into electrical energy to supply the electrical energy to the electricity storing means 2, and as shown in FIG. 3, is provided with a shaft member 3b to which a stator 3a is fixed, and a rotor 3c which is rotatably attached to the shaft member 3b and is connected with the pulley 55 as a unit.

Figure 4:
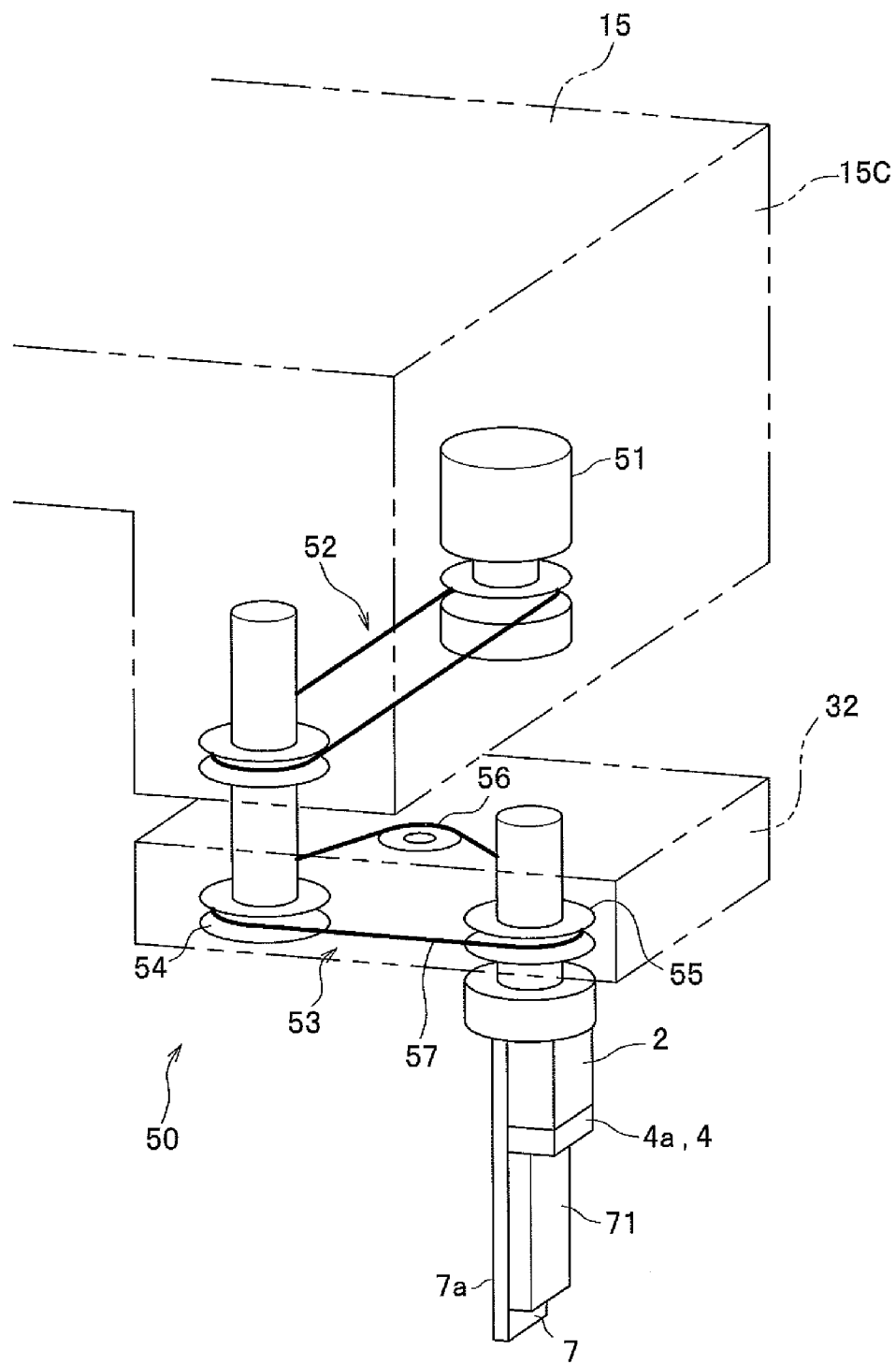
FIG. 4 is a schematic perspective view showing a motion of an electricity generating device.

As shown in FIG. 4, the generator 3 utilizes rotational energy which is used to rotate the X-ray imaging member 7 by the servomotor 51, causes the rotor 3c connected with the pulley 55 as a unit to rotate around the stator 3a to generate electricity, and supplies the electricity to the electricity storing means 2.

By this configuration, since the rotor 3c of the generator 3, the electricity storing means 2 and the X-ray imaging member 7 are rotated as a unit, it is possible to certainly prevent disconnection and/or bad connection of wires in the case of causing the X-ray imaging member 7 to perform the local movement different from the revolving movement.

Note that although the present embodiment adopts the generator 3 as the electric power supplying means, it is not limited to the generator 3. The present embodiment can also adopt a photoelectric conversion means 3' (see FIG. 6A) that converts light energy into electrical energy, and/or a wireless power transmission system 3" (see FIG. 6B).

As the photoelectric conversion means 3', a photoelectric conversion element such as a photodiode, a solar cell or the like, is appropriately adopted.

The wireless power transmission system 3" is a system that wirelessly transmits electric power without using a metal contact and/or a connector. As the wireless power transmission system 3", various systems making use of a non-contact charging technique utilizing electromagnetic induction and used at close range, an electromagnetic wave resonance technique utilizing resonant induction, a radio wave transmission technique utilizing radio waves to enable a long-distance electric power transmission, and the like, are appropriately adopted depending on the intended use.

The data detection circuit 71 is a circuit that converts the X-ray flux Xa received at the acceptance surface 7a into image data, and is disposed on the X-ray imaging member 7 as a unit.

The transmitting and receiving device 4 is provided with the sensor unit transmitting and receiving device 4a that is disposed on the X-ray imaging member 7 as a unit in the main body apparatus 200, and the main body transmitting and receiving device 4b provided in the main body control unit 400, and wirelessly communicates data between the main body control unit 400 (specifically, an image processing device (I.P.) 65 as described later) and the data detection circuit 71. Note that "wireless" means not connecting by means of a cable or the like via a metal contact and/or a connector, and means communicating by means of radio waves and/or infrared rays.

The transmitting and receiving device 4 wirelessly transmits image data detected by the detection circuit 71, from the sensor unit transmitting and receiving device 4a disposed on the sensor unit 210 (see FIG. 5) in the main body apparatus 200, to the main body transmitting and receiving device 4b provided in the main body control unit 400, and the transmitted image data is processed in the image processing device 65.

Moreover, the transmitting and receiving device 4 receives a sampling clock signal (image acquisition signal) at the sensor unit transmitting and receiving device 4a. More specifically, when the sensor unit transmitting and receiving device 4a wirelessly transmits the image data to the main body transmitting and receiving device 4b, the main body transmitting and receiving device 4b transmits an image acquisition signal (transmission request signal for next image) which informs a receipt of one image, to the sensor unit transmitting and receiving device 4a. Then, the sensor unit transmitting and receiving device 4a responds to the transmission request signal to transmit the next, second image data to the main body transmitting and receiving device 4b. Thus, the sensor unit transmitting and receiving device 4a and the main body transmitting and receiving device 4b repeats the transmitting and receiving.

<Main body control unit>

The main body control unit 400 is provided with a motion control device 60 that controls the revolution driving device 20, the imaging-side driving device 30 and X-ray imaging of the subject K, an image processing device 65 that processes image data acquired by the X-ray imaging member 7, an operation unit (OPE.) 68 that is operated by an operator, the main body transmitting and receiving device 4b that constitutes the transmitting and receiving device 4, and a display unit (not shown) that displays an image detected by the X-ray imaging member 7.

The motion control device 60 is provided with a detection unit (DET) 61 including a position detecting means (for example, constituted by an encoder) that detects the revolution position P of the slit 12a and the acceptance surface 7a (accordingly, which is also the revolution position P of the arm 15) and the rotational position (namely, which is the position on the movement path M) of the X-ray imaging member 7 with the rotation center line Lc as the center, respectively, and a motion control unit (M.C.) 62 including a central processing unit. The motion control unit 62 controls actuation of each of the servo motors 21, 31, 47 and 51 in response to signals set by the operation unit 68 and detection signals from the detection unit 61.

The image processing device 65 processes image data acquired through X-ray imaging by the X-ray imaging member 7 to generate CT image, panoramic image and cephalic image.

Moreover, performed through the operation unit 68 are switching of each radiography mode of CT imaging, panoramic radiography and cephalic radiography of the subject K, settings of the predetermined distance d2, an initial revolution position P of the arm 15 at the start of radiography and a shift revolution amount S as described later, and the like.

Next, the motion of the radiographic X-ray equipment 1 will be described, giving an example of the case of performing CT imaging by means of the radiographic X-ray equipment 1, with reference to FIGS. 1 and 8.

When the CT imaging is selected by the operation unit 68, the slit 12a and the acceptance surface 7a (accordingly, the arm 15) occupy a first shift revolution position Ps1 as the initial revolution position in the circumferential direction of the revolution center line La. At the first shift revolution position Ps1, the X-ray imaging member 7 is driven by the servo motor 31 to rotate in the rotational direction (the clockwise direction in FIGS. 8A and 8B) from the first position set as the initial position on the movement path M of the local rotational movement, and moves on the movement path M to make one continuous revolution around the rotation center line Lc. Meanwhile, under control of the motion control device 60, the X-ray imaging member 7 detects the X-ray flux Xa via the acceptance surface 7a to perform X-ray imaging, at every position of predetermined intervals (for example, predetermined rotational angles in the local rotational movement), thereby acquiring a shift image data group comprised of multiple image data at each position on the movement path M.

The image processing device 65 performs image correction processing for correcting image data acquired at each position on the movement path M, in order to acquire images for a virtual X-ray imaging member 70 as described later, with the first shift revolution position Ps1 as the start, at a plurality of shift revolution positions Ps while the X-ray imaging member 7 makes one or more revolutions with the revolution center line La as the center.

Figure 8:
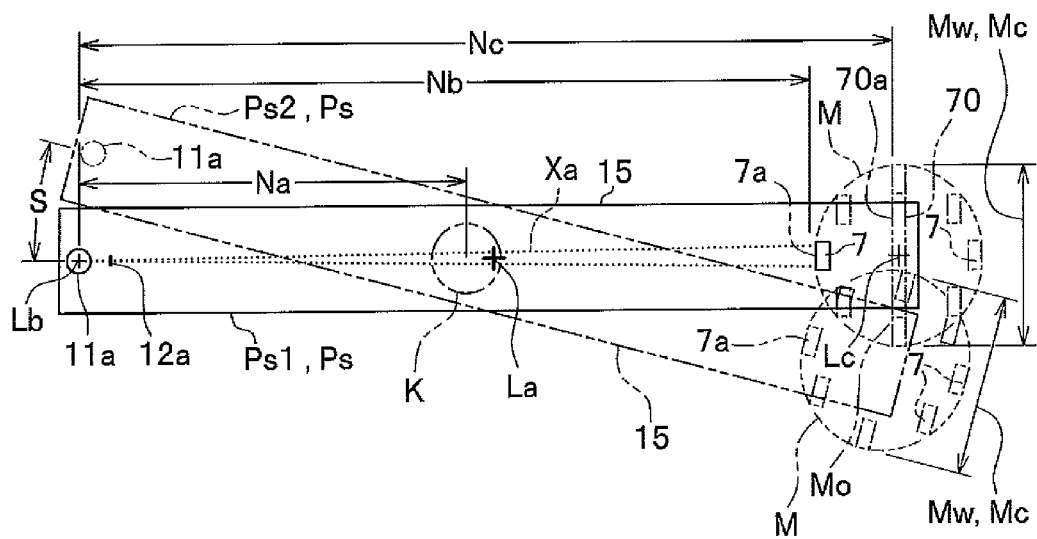
FIG. 8 is a top plan view in a schematic view showing main parts for explaining the revolving movement and the local rotational movement when CT imaging is performed by the radiographic X-ray equipment in FIG. 1.

As shown in FIG. 8, when the virtual X-ray imaging member 70 has a planate acceptance surface 70a (hereinafter referred to as "virtual acceptance surface 70a") with a circumferential direction width (a width in the predetermined direction) equal to, for example, the movement width Mw, the image processing device 65 performs image correction processing with respect to image data acquired by the X-ray imaging member 7, based on a scaling rate N calculated by the following formula.

$$N=(Nc/Na)/(Nb/Na)=Nc/Nb$$

Here, Na represents a distance between the X-ray source 11a and an X-ray imaging site in the subject K; Nb represents a distance between the X-ray source 11a and the acceptance surface 7a; and Nc represents a distance between the X-ray source 11a and the virtual acceptance surface 70a.

Note that, also in the case where the virtual X-ray imaging member 70 has an arc-shaped acceptance surface 7a with the radiation centerline Lb as the center, a CT image can be acquired by a similar image correction processing using the scaling rate N.

Moreover, when the X-ray imaging member 7 makes one revolution around the rotation center line Lc as the center, the servo motor 21 causes the arm 15 to perform a shift revolution movement in steps of shift revolution amount S, which is smaller than one revolution of the revolution movement, in the revolution direction (the clockwise direction in FIGS. 8A and 8B) so that the slit 12a and the acceptance surface 7a occupy a second shift revolution position Ps2. By the shift revolution movement of the arm 15, the slit 12a and the acceptance surface 7a move from the first shift revolution position Ps1 to the second shift revolution position Ps2.

Here, in the transient duration in which the slit 12a and the acceptance surface 7a move from the first shift revolution position Ps1 to the second shift revolution position Ps2, the X-ray imaging member 7 continues the local rotational movement without performing a temporary stop and a restart after the temporary stop, but no X-ray imaging is performed. Note that, as another example, the driving devices 20,30 may be configured to cause the X-ray imaging member 7 to finish X-ray imaging in the revolution range of less than one revolution at the shift revolution position Ps1, and to cause the arm 15 to perform a shift revolving movement to the next shift revolution position Ps in the remaining revolution range of the one revolution. Thus, the X-ray imaging member 7 continues the local rotational movement until the CT imaging is finished.

Referring to FIG. 8, in the shift revolution positions Ps adjacent to each other in the circumferential direction, the shift revolution amount S is set to form an overlap range Mo in which circumferential direction movement ranges Mc (equal to the movement width Mw in this embodiment) of the respective local rotational movements at the adjacent shift revolution positions Ps overlap each other in the circumferential direction. The motion control device 60 controls the X-ray imaging member 7 to acquire different shift image data groups of the subject K at a plurality of different positions on the movement path M of the X-ray imaging member 7 by the local rotational movement, in the circumferential direction movement range Mc of the local movement at each shift revolution position Ps.

Here, the respective shift revolution amounts S are set to be a value identical to each other in this embodiment, but may be set to be two or more values different from each other in another example.

The slit 12a and the acceptance surface 7a move from the first shift revolution position Ps1 to the second shift revolution position Ps2, and further the slit 12a and the acceptance surface 7a perform a shift revolving movement sequentially in steps of the shift revolution amount S in the revolution direction to make one revolution around the revolution center line La, thereby finishing the CT imaging.

Then, the image processing device 65 collects the shift image data group at each shift revolution position Ps to generate the entire image.

Note that, also in the case where the radiographic X-ray equipment 1 performs panoramic radiography and cephalic radiography, the X-ray imaging member 7 that performs the local rotational movement performs the radiography in the same manner as in the CT imaging, at one or more shift revolution positions Ps, by using the XY table 22 as necessary.

Next, description is given of the operation and advantageous effects of the first embodiment configured as described above.

The radiographic X-ray equipment 1 is provided with the imaging-side driving device 30 that causes the X-ray imaging member 7 which is a driven member to perform the local movement different from the revolving movement of the arm 15, in the movement width Mw of the acceptance surface 7a when the predetermined direction is defined by the circumferential direction relative to the revolution center line La. The width W2 of the acceptance surface 7a in the predetermined direction is smaller than the movement width Mw, and the local movement is the local rotational movement with the rotation center line Lc as the center.

According to this configuration, since the width W2 of the acceptance surface 7a in the predetermined direction is small as compared to the movement width Mw of the local rotational movement of the acceptance surface 7a driven by the imaging-side driving device 30, an inexpensive X-ray imaging member 7 can be used as compared to an X-ray imaging member having an acceptance surface of a size corresponding to the movement width Mw, thereby enabling a reduction in cost of the radiographic X-ray equipment 1.

Moreover, since the X-ray imaging member 7 performs the rotational movement, it is possible to make unnecessary a temporary stop which would be generated when the X-ray imaging member 7 is subjected to an arc movement or a linear movement, and/or an operation for restarting after the temporary stop. As a result, it is possible to decrease acceleration and deceleration which act on the X-ray imaging member 7, and accordingly to reduce inertial force due to the acceleration and deceleration. Consequently, it is possible to reduce vibration of the driven member due to the inertial force and to improve durability of the X-ray imaging member 7 of an elongated shape. Furthermore, it is possible to suppress a decrease in speed due to a temporary stop of the X-ray imaging member 7 for the duration of the start to the end of the X-ray imaging, and/or an operation for restarting, and accordingly to improve an efficiency in X-ray imaging work by speed-up of the X-ray imaging member 7.

When the X-ray imaging member 7 makes one revolution with the rotation center line Lc as the center, the rotation center line Lc is arranged so that the subject K is positioned at all times between the X-ray irradiating member 10 and the X-ray imaging member 7. Accordingly, at an arbitrary time or in a continuous period in the duration in which the X-ray imaging member 7 makes one revolution with the rotation center line Lc as the center, the X-ray imaging becomes possible by means of the X-ray imaging member 7, which improves an efficiency in the X-ray imaging work The revolution driving device 20 causes the X-ray irradiating member 10 and the X-ray imaging member 7 to perform the shift revolution movement in steps of the shift revolution amount S, which is smaller than one revolution of the revolution movement, so that the X-ray irradiating member 10 and the X-ray imaging member 7 occupy the shift revolution positions Ps1, Ps2. The imaging-side driving device 30 causes the X-ray imaging member 7 to perform the local rotational movement at each shift revolution position Ps1, Ps2. The shift revolution positions Ps1, Ps2 adjacent to each other in the circumferential direction are positions that form the overlap range Mo in which the circumferential direction movement ranges Mc of the local rotational movements at the respective positions overlap each other in the circumferential direction.

This makes it possible to perform CT imaging, panoramic radiography and cephalic radiography, using the X-ray imaging member 7 in which the width of the acceptance surface 7a in the above predetermined direction is smaller than the movement width Mw of the X-ray imaging member 7.

The imaging-side driving device 30 is provided with the distance adjusting mechanism 49 which can change the distance d1 between the rotation center line Lc and the acceptance surface 7a of the X-ray imaging member 7. Accordingly, it is possible to change the radiographic area on the acceptance surface 7a by changing the distance d1 between the rotation center line Lc and the X-ray imaging member 7, without changing the shift revolution amount S, which improves convenience of the radiographic X-ray equipment 1.

The slit member 12 of the X-ray irradiating member 10 includes the collimator 12c that defines the irradiation range and the irradiation direction of the X-ray flux Xa which is irradiated on the subject K, and the collimator 12c moves to follow the acceptance surface 7a of the X-ray imaging member 7 which performs the local rotational movement, so as to keep the state in which the collimator 12c, the subject K and the acceptance surface 7a are positioned in alignment with one another.

By this configuration, since the collimator 12c moves to follow the acceptance surface 7a while keeping the state in which the collimator 12c, the subject K and the acceptance surface 7a are positioned in alignment with one another, it is possible to accurately direct the X-ray flux Xa in the irradiation range and the irradiation direction defined by the collimator 12c, toward the subject K and the acceptance surface 7a, and thus to improve accuracy of the radiography.

Moreover, the radiographic X-ray equipment 1 according to the first embodiment of the present invention causes the electricity storing means 2, the X-ray imaging member 7, the data detection circuit 71 and the sensor unit transmitting and receiving device 4a to perform the local movement (rotation movement) as a unit without moving relative to one another, thereby making it possible to certainly prevent disconnection and/or bad connection of wires between the electricity storing means 2 and the X-ray imaging member 7, the data detection circuit 71 and the sensor unit transmitting and receiving device 4a.

Accordingly, the radiographic X-ray equipment 1 according to the first embodiment of the present invention makes it possible, while causing the X-ray imaging member 7 to perform the local movement different from the revolving movement to thereby acquire a broad acceptance surface and accomplish cost reduction of the radiographic X-ray equipment 1, to suppress generation of bad connection of a cable and/or noises in the case of causing the X-ray imaging member 7 to perform the local movement different from the revolving movement, and to accomplish improvement in reliability and durability.

In addition, the radiographic X-ray equipment 1 according to the first embodiment of the present invention wirelessly performs transmitting and receiving between the data detection circuit 71 and the main body control unit 400, thereby making it possible to comprehensively suppress generation of bad connection of a cable and/or noises and to ensure high reliability and durability.

A modified example of the first embodiment and a second embodiment will be hereinafter described with reference to FIGS. 9, 10A and 10B. The second embodiment differs from the first embodiment in portions of the configuration and has basically the same configuration as to the other portions. Accordingly, description of the same portion is omitted or simplified, and description is given focusing on different portions. Note that, as to the same member as or the member corresponding to the member in the first embodiment, the same reference sign has been used as necessary.

According to the modified example of the first embodiment and the second embodiment, it is possible to accomplish the like operation and advantageous effects as in the first embodiment, based on the like configuration as in the first embodiment.

Figure 9:
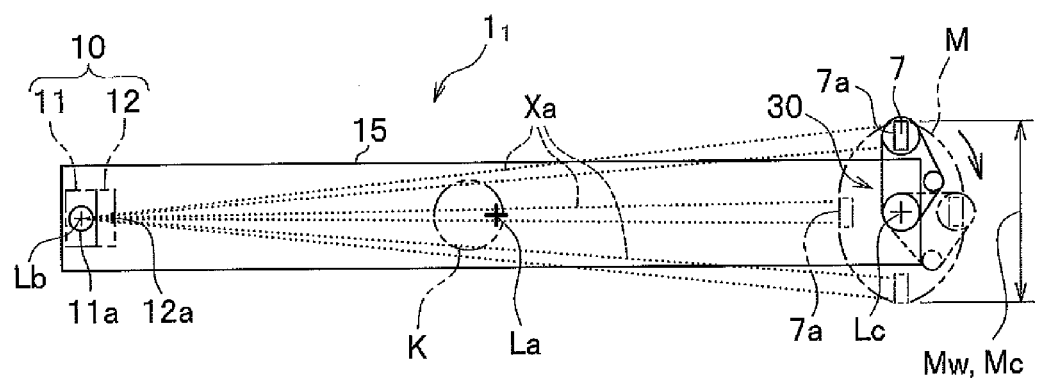
FIG. 9 is a view illustrating a first modified example of the first embodiment of the present invention and corresponding to FIG. 7A.

Referring to FIGS. 2A, 2B and 9, in the X-ray imaging member 7 of a radiographic X-ray equipment 11 according to a first modified example of the first embodiment, the servo motor 47 of the distance adjusting mechanism 49 is controlled by the motion control device 60 to change the length of the connecting member 43 to thereby change the distance d1 and the predetermined distance d2, depending on the position on the movement path M of the X-ray imaging member 7 by the local rotational movement. This makes the local rotational movement of the X-ray imaging member 7, for example, a circular movement which is flattened in the radial direction or in the irradiation direction with the revolution center line La as the center. This flattened circular movement includes, for example, an elliptic movement and an oval movement. Here, the oval movement is, unlike the elliptic movement, a movement comprised of a pair of nearly linear movements which face each other across the rotation center line Lc in the radial direction with the revolution center line La as the center, and of a pair of nearly semicircular movements which link to the pair of nearly linear movements, respectively, and face each other in the circumferential direction with the revolution center line La as the center.

Moreover, the distance d1 and the predetermined distance d2 are changed by the distance adjusting mechanism 49 depending on the position on the movement path M, thereby making it possible to set the movement path M according to a shape of the subject K.

Thus, the distance adjusting mechanism 49 changes the distance d1 or the predetermined distance d2 depending on the position of the X-ray imaging member 7 on the movement path M, thereby making it possible to make the distance d1 or the predetermined distance d2 between the subject K and the X-ray imaging member 7 different depending on the position of the X-ray imaging member 7 on the movement path M, during the local rotational movement of the X-ray imaging member 7 or the revolving movement thereof. Accordingly, setting of the movement path M according to a shape of the subject K becomes possible and convenience of the radiography is improved.

Moreover, by making the local rotational movement of the X-ray imaging member 7 the circular movement which is flattened in the irradiation direction, it is possible to reduce a fluctuating range of the scaling rate N for correcting image data acquired by the X-ray imaging member 7 and accordingly an improvement in accuracy of the radiography becomes possible.

The second embodiment will be described with reference to FIGS. 10A and 10B.

Figure 10A:
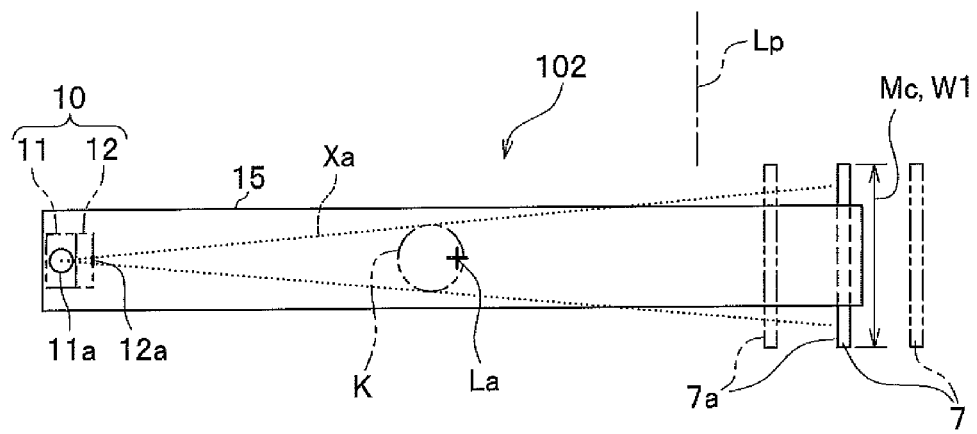
FIGS. 10A and 10B are views illustrating a second embodiment of the present invention, where FIG. 10A corresponds to FIG. 7A and FIG. 10B corresponds to FIG. 7B.

In radiographic X-ray equipment 102 according to the second embodiment, the rotation center line Lc of the local rotational movement is nearly parallel with a specific line Lp (FIG. 10A shows, as an example, a specific line Lp nearly perpendicular to a plane which contains the revolution center line La and the X-ray source 11a) which is parallel with an orthogonal line as a crossed line intersecting with the revolution center line La (namely, a line perpendicular to the revolution center line La). Accordingly, in the local rotational movement, the acceptance surface 7a rotates with its longitudinal direction being nearly parallel with the specific line Lp, accordingly with an elongated state in the orthogonal direction relative to the revolution center line La.

Moreover, in the radiographic X-ray equipment 102, the predetermined direction is the revolution center line direction and accordingly the movement width Mw of the local rotational movement is the width in the revolution center line direction. Also, the circumferential direction movement range Mc is equal to the width in the circumferential direction of the acceptance surface 7a, in this example, the width W1 in its longitudinal direction.

Figure 10B:
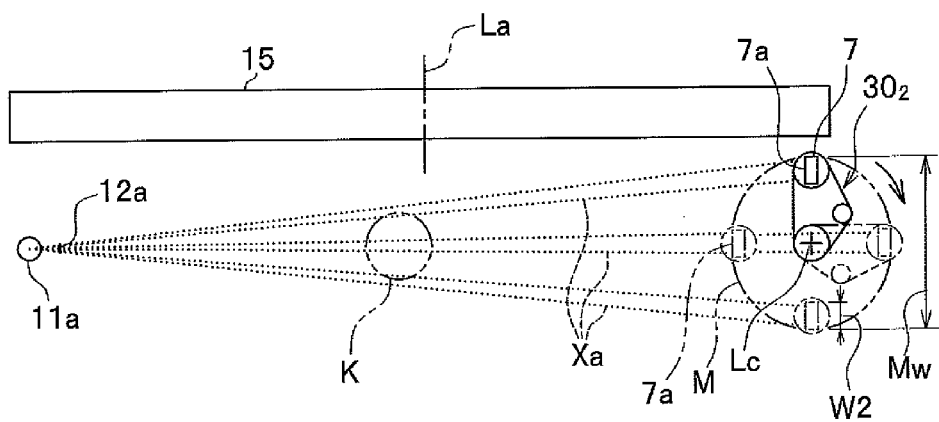

Referring to FIGS. 10A and 10B, the radiographic X-ray equipment 102 of the second embodiment corresponds to the first embodiment and is provided with, as the secondary driving device, an imaging-side driving device 302 having basically the same configuration as the imaging-side driving device 30 (see FIGS. 2A and 2B) in the first embodiment. The imaging-side driving device 302 causes the X-ray imaging member 7 to perform the local rotational movement with the rotation center line Lc which is nearly parallel with the specific line Lp, as the center.

Hereinafter, description is given of modified configuration of embodiments which could be implemented by modifying portions of the configuration of the embodiments described above.

The time of radiography by the radiographic X-ray equipment maybe a time at which the revolution angle by the revolving movement of the arm 15 is 180° or less.

When the driven member makes one revolution with the rotation center line Lc as the center, the rotation center line Lc may be arranged so that the subject K is positioned between the X-ray irradiating member 10 and the X-ray imaging member 7 only in a limited range of less than one revolution.

In the second embodiment, the crossed line intersecting with the revolution center line La may intersect with the revolution center line La in the form other than the orthogonal.

The supporting member supporting the X-ray irradiating member 10 and the X-ray imaging member 7 may be constituted by separate supporting bodies that support the X-ray irradiating member 10 and the X-ray imaging member 7, respectively. Moreover, in this case, the revolution center line La may be set separately for the X-ray irradiating member 10 and the X-ray imaging member 7.

The radiographic X-ray equipment may be used in medical care other than dental examination. Moreover, the target may be an object other than human and accordingly the radiographic X-ray equipment may be used in examination of the object.

<Third Embodiment>

The third embodiment differs from the first embodiment and the second embodiment in which the local movement is a rotational movement, in that the local movement is an arc-shaped reciprocating movement (arc movement). Likewise even in the case of arc movement, the generator 3 (see FIG. 11) converts rotational energy by the arc movement into electrical energy to make it possible to drive the X-ray imaging member 7 and the like.

Accordingly, in the description below, description is given of constituent elements primarily associated with the arc movement different from the first embodiment, and the like constituent element as in the first embodiment is given the same reference sign and detailed description thereof is omitted.

Figure 11:
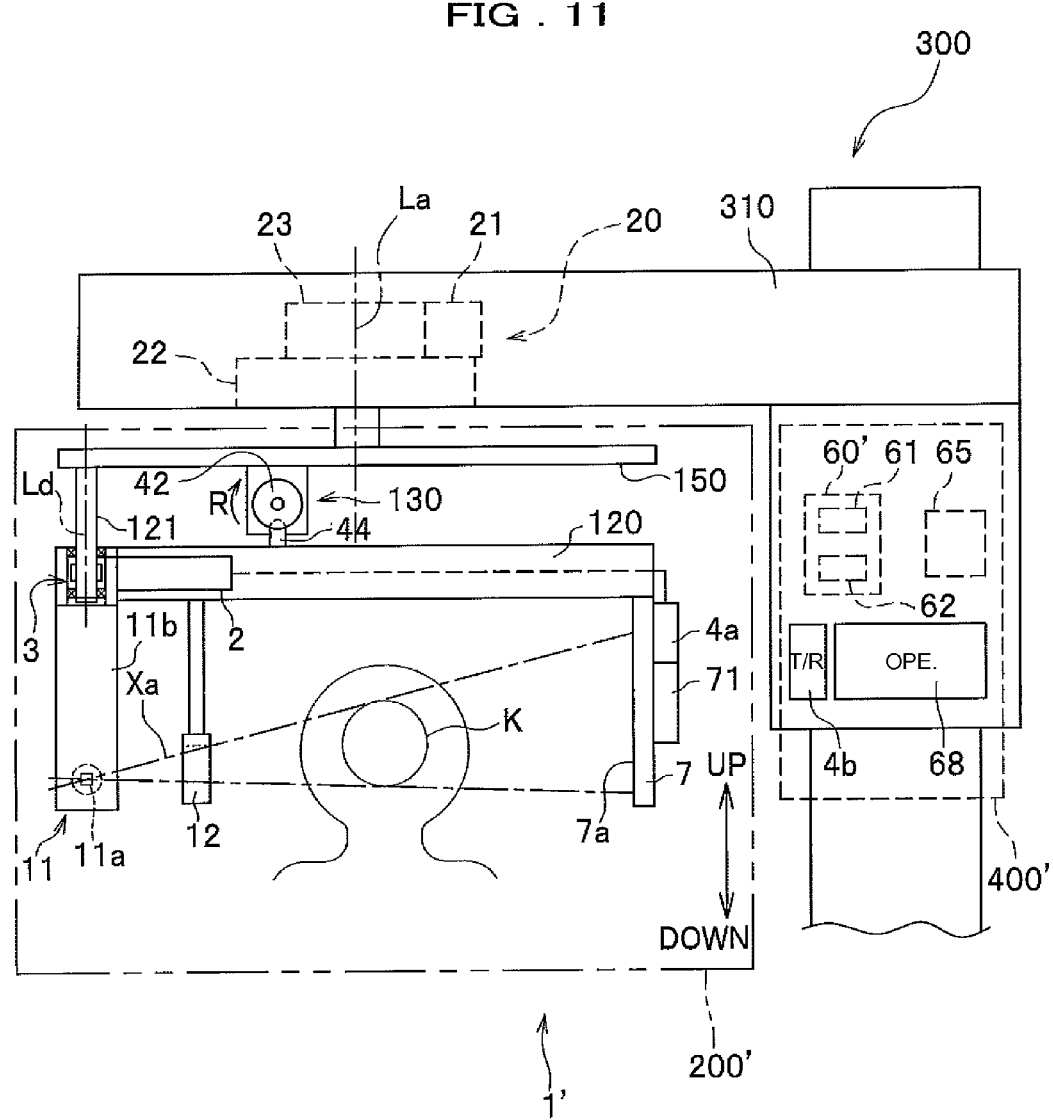
FIG. 11 is a front view showing an example of application, in the case where the local movement is an arc movement, of an X-ray imaging member according to a third embodiment of the present invention.

As shown in FIG. 11, radiographic X-ray equipment 1' according to the third embodiment is provided with an X-ray radiating member 11 having an X-ray source 11a, a slit member 12 that forms X-ray flux from the X-ray source 11a into a slit-shaped X-ray flux Xa, an X-ray imaging member 7 that detects the X-ray flux Xa, an arc movement arm 120 that supports the X-ray radiating member 11 and the X-ray imaging member 7, a revolution driving device 20 that causes the arc movement arm 120 to rotate around the revolution center line La, an arc movement means 130 by a cam mechanism that causes the X-ray imaging member 7 to perform an arc movement around an arc movement center axis Ld, and a motion control device 60' that controls motions of the revolution driving device 20 and the arc movement means 130 by the cam mechanism.

The X-ray imaging member 7 is provided on the arc movement arm 120 and in the same manner as the first embodiment, the sensor unit transmitting and receiving device 4a and the data detection circuit 71 are provided on the X-ray imaging member 7 as a unit.

The arc movement arm 120 is rotatably supported by a shaft member 121 arranged on the arc movement center axis Ld. The arc movement center axis Ld is arranged coaxially with the X-ray radiating member 11 provided on the arc movement arm 120.

Moreover, the generator 3 is attached to the shaft member 121 arranged on the arc movement center axis Ld, and the electricity storing means 2 is provided on the arc movement arm 120.

As shown in FIG. 12B, the arc movement means 130 by the cam mechanism is provided with a cam roller 132 which is connected to a servomotor 131 and is rotatably supported, a cam groove 133 which is formed on the outer periphery of the cam roller 132, and a cam pin 134 which is engaged to move along the cam groove 133.

The cam pin 134 is fixed to project from the arc movement arm 120. Moreover, the arc movement means 130 by the cam mechanism is provided on an arm 150 so that the cam pin 134 is engaged with the cam groove 133.

Figure 13A:
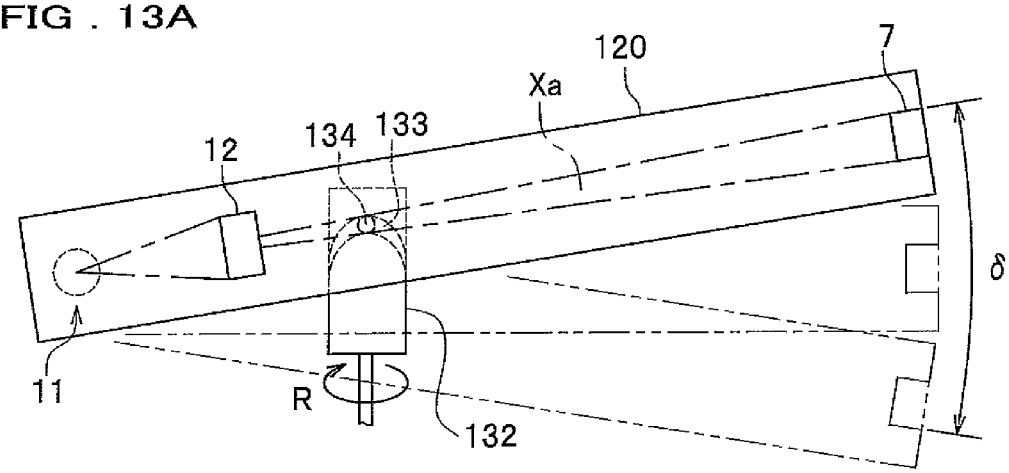
FIGS. 13A to 13C are bottom views showing motions of the arc movement means according to the third embodiment of the present invention, where
Figure 13B:
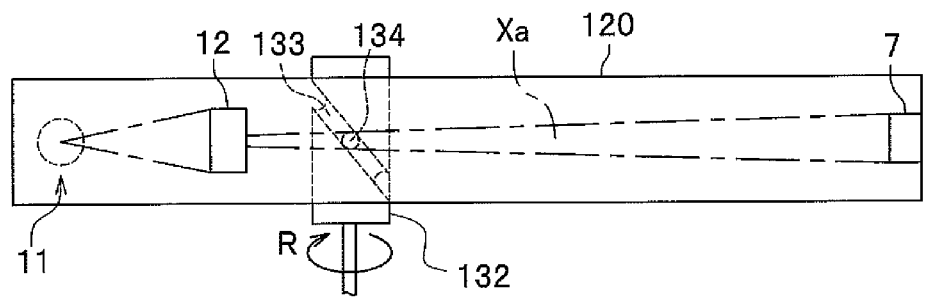
Figure 13C:
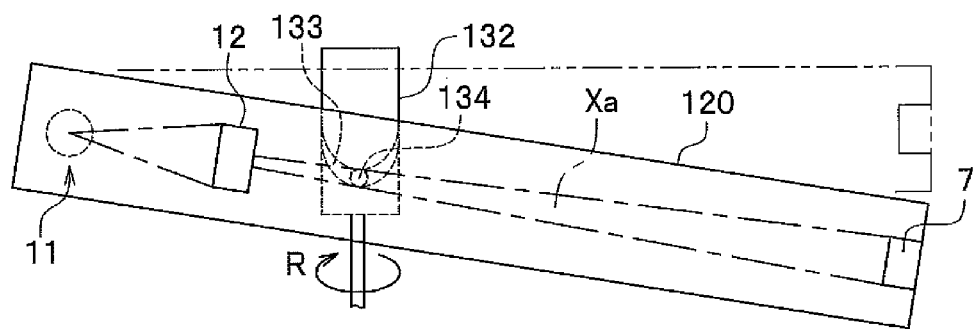
Figure 14:
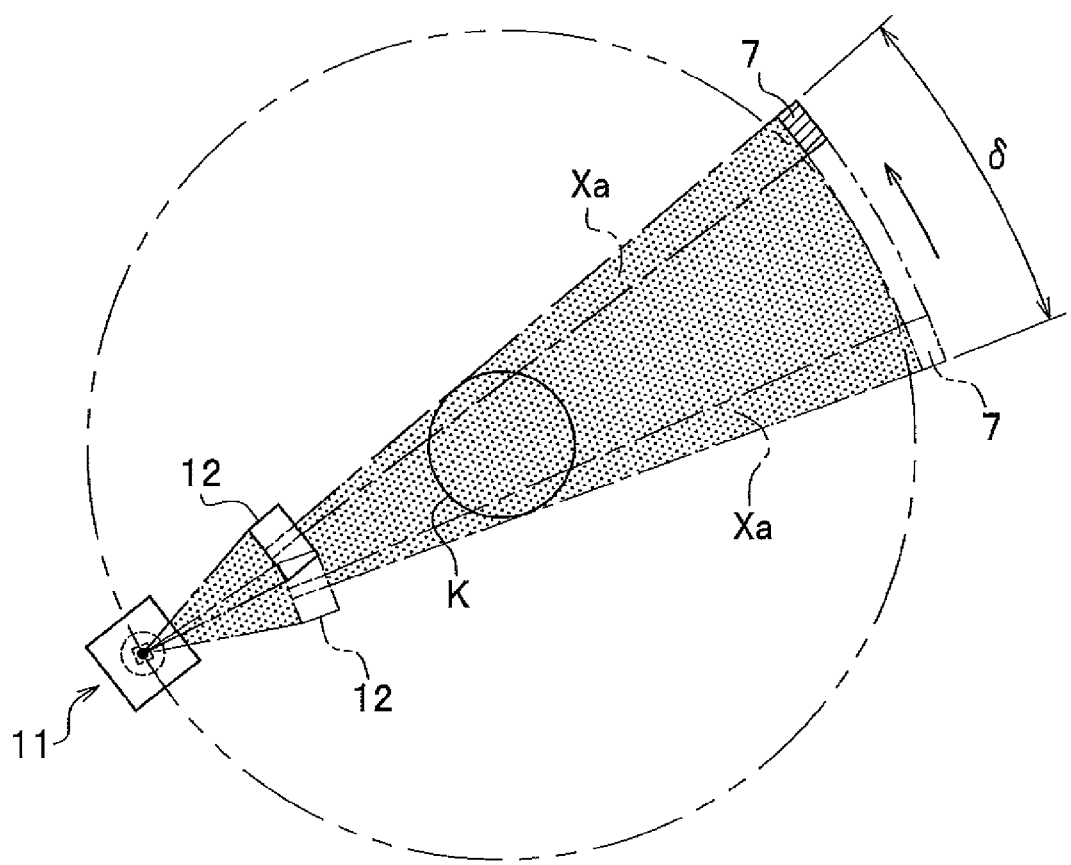
FIG. 14 is a plan view showing a motion of the X-ray imaging member according to the third embodiment of the present invention.

By this configuration, as shown in FIGS. 13A to 13C, the radiographic X-ray equipment 1' according to the third embodiment causes the servo motor 131 to rotate the cam roller 132 in an R direction to thereby rotate the arc movement arm 120 with the arc movement center axis Ld as the center and cause the X-ray imaging member 7 to perform the arc movement in an arc movement range δ (FIG. 13A) so as to detect the X-ray flux Xa transmitted through the subject K, thereby making it possible to have the X-ray imaging member 7 function as a broad two-dimensional X-ray imaging member in the arc movement range δ.

Moreover, since the generator 3 attached to the shaft member 121 arranged on the arc movement center axis Ld, the electricity storing means 2 and the X-ray imaging member 7 perform the arc movement as a unit, it is possible to certainly prevent disconnection and/or bad connection of wires by driving the X-ray imaging member 7 with the electricity storing means 2.

Note that although in the third embodiment too, description has been given of the example adopting the generator 3 as the electric power supplying means, it is also possible to adopt the photoelectric conversion means 3' and/or the wireless power transmission system 3" in the same manner as the first embodiment.

Moreover, although the radiographic X-ray equipment 1 and the like according to the present invention supplies electric power from the electric power supplying means such as the generator 3 to the electricity storing means 2 to thereby suppress bad connection or the like of a cable in the case of causing the X-ray imaging member 7 to perform a local movement different from a revolving movement, the present invention is not limited to the electric power supplying means such as the generator 3, nor limited to the time of radiography. For example, a configuration may be adopted in which the main body control unit 400 and the electricity storing means 2 are wired to be able to be disconnected from each other (by a switching circuit, manual operation or the like), and at the time of non-radiography, an external power source or the like that supplies electric power to the main body control unit 400 is used to charge the electricity storing means 2, and at the time of radiography, the external power source or the like that supplies electric power to the main body control unit 400, and the electricity storing means 2 are disconnected from each other to prevent twist of a cable and/or noises.

REFERENCE SIGNS LIST 1, 1', 11, 102 Radiographic X-ray equipment
2 Electricity storing means
3 Generator
3' Photoelectric conversion means
3" Wireless power transmission system
4 Transmitting and receiving device
4a Sensor unit transmitting and receiving device
4b Main body transmitting and receiving device
7 X-ray imaging member
7a Acceptance surface
10 X-ray irradiating member
13 Driving member
15 Arm
20 Revolution driving device
22 XY table
30, 302 Imaging-side driving device
60, 60' Motion control device
61 Detection unit
62 Motion control unit
65 Image processing device
68 Operation unit
200 Main body apparatus
210 Sensor unit
300 Supporting apparatus
400 Main body control unit
La Revolution center line
Lc Rotation center line
M Movement path
Mw Movement width
Ps Shift revolution position
S Shift revolution amount
Mc Circumferential direction movement range
Mo Overlap range
K Subject
Xa X-ray flux

The invention claimed is:

1. Radiographic X-ray equipment including an X-ray irradiating member that irradiates a subject with an X-ray flux, an X-ray imaging member with an acceptance surface provided for receiving the X-ray flux transmitted through the subject, a revolution driving device that causes the X-ray irradiating member and the X-ray imaging member to perform a revolving movement around the subject with a revolution center line as the center, and a main body control unit that controls the revolution driving device, the radiographic X-ray equipment comprising:
a secondary driving device that is controlled by the main body control unit to cause the X-ray imaging member to perform a local movement different from the revolving movement, with a movement width in a predetermined direction;
an electricity storing means that stores electric power to be supplied to the X-ray imaging member; and
an electric power supplying means that supplies electric power to the electricity storing means,
the X-ray imaging member and the electricity storing means being connected to each other, and the secondary driving device causing the electricity storing means and the X-ray imaging member to perform the local movement as a unit without moving relative to each other, and
wherein the electric power supplying means includes an electricity generating means that is connected by wire with the electricity storing means, the electricity generating means is provided at a position to perform a local movement as a unit without moving relative to the electricity storing means and the X-ray imaging member, the local movement is a rotational movement, and the electricity generating means utilizes a rotational force by the rotational movement to generate electricity.

2. The radiographic X-ray equipment according to claim 1, wherein the electric power supplying means includes a wireless power transmission device that wirelessly transmits electric power to the electricity storing means.

3. The radiographic X-ray equipment according to claim 1, wherein the electricity generating means includes a photoelectric conversion means that converts light energy into electrical energy.

4. The radiographic X-ray equipment according to claim 2, further comprising:
a data detection circuit that detects an X-ray flux received by the X-ray imaging member, as image data;
an image processing device that is provided in the main body control unit and processes the image data detected by the data detection circuit; and
a transmitting and receiving device that wirelessly communicates data between the image processing device and the data detection circuit.

5. The radiographic X-ray equipment according to claim 1, further comprising:
a data detection circuit that detects an X-ray flux received by the X-ray imaging member, as image data;
an image processing device that is provided in the main body control unit and processes the image data detected by the data detection circuit; and
a transmitting and receiving device that wirelessly communicates data between the image processing device and the data detection circuit.

6. The radiographic X-ray equipment according to claim 3, further comprising:
a data detection circuit that detects an X-ray flux received by the X-ray imaging member, as image data;
an image processing device that is provided in the main body control unit and processes the image data detected by the data detection circuit; and
a transmitting and receiving device that wirelessly communicates data between the image processing device and the data detection circuit.

* * * * *